US012619702B2

(12) United States Patent
Moulton et al.

(10) Patent No.: US 12,619,702 B2
(45) Date of Patent: May 5, 2026

(54) SECURE USER AUTHENTICATION FOR MEDICAL DEVICE CONSOLES

(71) Applicant: Boston Scientific Scimed, Inc., Maple Grove, MN (US)

(72) Inventors: Heather Moulton, White Bear Lake, MN (US); Jim Sievert, Bradenton, FL (US); Jeffry V. Marshik, New Brighton, MN (US); Matthew J. Edelman, Blaine, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 62 days.

(21) Appl. No.: 18/645,085

(22) Filed: Apr. 24, 2024

(65) Prior Publication Data

US 2024/0370549 A1    Nov. 7, 2024

Related U.S. Application Data

(60) Provisional application No. 63/499,575, filed on May 2, 2023.

(51) Int. Cl.
| | |
|---|---|
| *G06F 21/36* | (2013.01) |
| *A61B 34/00* | (2016.01) |
| *G16H 40/40* | (2018.01) |
| *G06F 21/34* | (2013.01) |
| *G16H 40/60* | (2018.01) |

(52) U.S. Cl.
CPC ............. *G06F 21/36* (2013.01); *A61B 34/25* (2016.02); *G16H 40/40* (2018.01); *G06F 21/34* (2013.01); *G16H 40/60* (2018.01)

(58) Field of Classification Search
CPC ......... G06F 21/36; G06F 21/34; G16H 40/40; G16H 40/60; A61B 34/25
See application file for complete search history.

(56) References Cited

U.S. PATENT DOCUMENTS

| | | | | |
|---|---|---|---|---|
| 9,419,799 | B1 | 8/2016 | Chung | |
| 10,453,572 | B1 * | 10/2019 | Brooks | ................. G16H 40/40 |
| 2009/0063187 | A1 * | 3/2009 | Johnson | ................ H04L 45/308 |
| | | | | 705/2 |
| 2011/0081888 | A1 * | 4/2011 | Waniss | .............. H04M 1/72409 |
| | | | | 455/66.1 |
| 2012/0165614 | A1 | 6/2012 | Strickland et al. | |

(Continued)

FOREIGN PATENT DOCUMENTS

CN        104468113 A      3/2015

OTHER PUBLICATIONS

"EPICENTER Concepts and Solutions Guide, Version 6.0", Internet Citation, Extreme Networks, Inc. pp. 9-267, Nov. 1, 2006. (Document is uploaded in 2 Parts).

(Continued)

*Primary Examiner* — Chau Le
(74) *Attorney, Agent, or Firm* — Seager Tufte & Wickhem, LLP

(57) ABSTRACT

A secure authentication scheme for a field service technician to access a device like a medical device in the field is provided. The system is arranged to authenticate an encrypted credential list using a public key from a public/private key pair and to authenticate a user to a device via SSH with a username and password combination stored in the encrypted credential list.

20 Claims, 7 Drawing Sheets

(56)     References Cited

U.S. PATENT DOCUMENTS

| | | | |
|---|---|---|---|
| 2012/0303385 A1* | 11/2012 | Darling ................. | G16H 20/13 |
| | | | 705/2 |
| 2014/0337922 A1* | 11/2014 | Sievert ................. | H04L 67/125 |
| | | | 726/3 |
| 2018/0365439 A1* | 12/2018 | Milman ................. | H04L 51/42 |
| 2019/0288860 A1* | 9/2019 | Poltorak .............. | H04L 9/3268 |
| 2019/0289013 A1* | 9/2019 | Makmel ............. | H04L 63/0876 |
| 2020/0365244 A1* | 11/2020 | Shah ..................... | G16H 80/00 |
| 2021/0272687 A1* | 9/2021 | Klopfenstein ........ | G06F 21/316 |
| 2022/0239662 A1 | 7/2022 | Conkle et al. | |
| 2022/0292221 A1* | 9/2022 | Sohail ................. | H04L 63/105 |
| 2024/0185996 A1* | 6/2024 | Grosskopf ............ | G16H 80/00 |

OTHER PUBLICATIONS

International Search Report and Written Opinion for International Application No. PCT/US2024/026051, dated Jul. 29, 2024.

\* cited by examiner

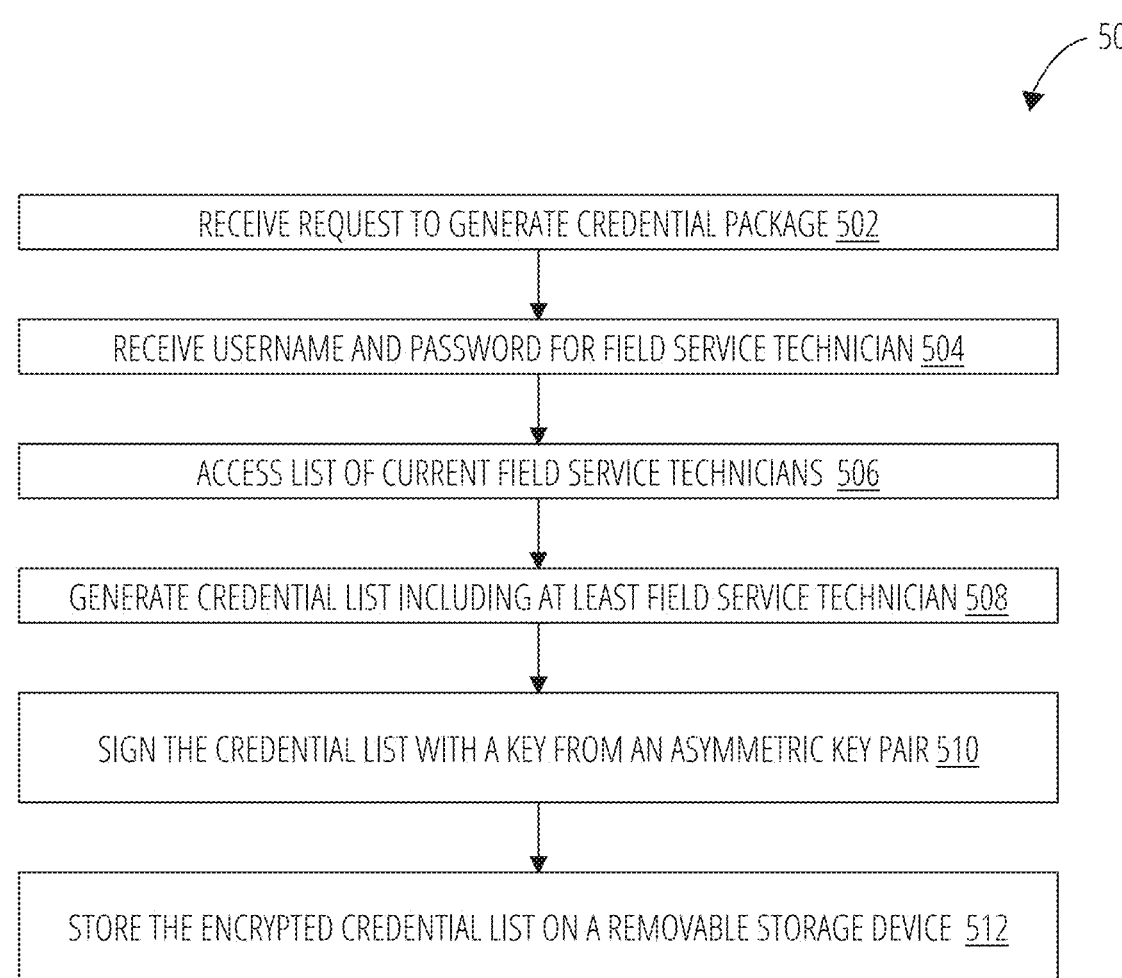

_500_

RECEIVE REQUEST TO GENERATE CREDENTIAL PACKAGE 502

RECEIVE USERNAME AND PASSWORD FOR FIELD SERVICE TECHNICIAN 504

ACCESS LIST OF CURRENT FIELD SERVICE TECHNICIANS 506

GENERATE CREDENTIAL LIST INCLUDING AT LEAST FIELD SERVICE TECHNICIAN 508

SIGN THE CREDENTIAL LIST WITH A KEY FROM AN ASYMMETRIC KEY PAIR 510

STORE THE ENCRYPTED CREDENTIAL LIST ON A REMOVABLE STORAGE DEVICE 512

FIG. 5

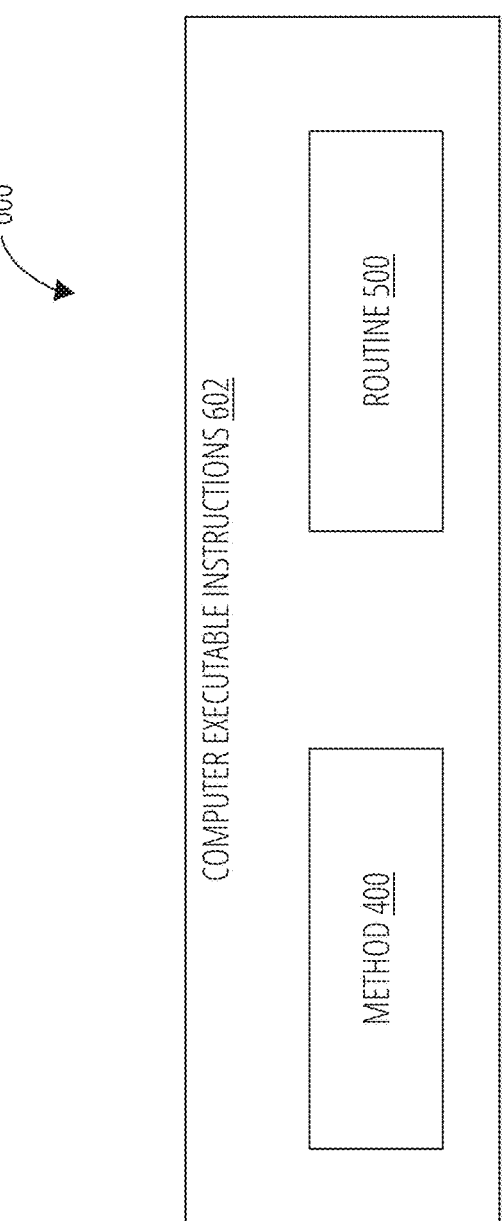
600
COMPUTER EXECUTABLE INSTRUCTIONS 602
ROUTINE 500
METHOD 400
FIG. 6

SECURE USER AUTHENTICATION FOR MEDICAL DEVICE CONSOLES

CROSS-REFERENCE TO RELATED APPLICATIONS

This application claims the benefit of U.S. Provisional Patent Application Ser. No. 63/499,575 filed on May 2, 2023, the disclosure of which is incorporated herein by reference.

TECHNICAL FIELD

The present disclosure pertains to securely accessing maintenance features of a medical device in the field.

BACKGROUND

Modern medical devices often include processing components and memory storing instructions executable by the processing components. The memory will also often store settings for the medical device as well as data related to the use and/or operation of the device. For example, the Angio-Jet™ Thrombectomy System is a peripheral thrombectomy device that delivers aspiration and a lytic delivery to treat a range of thrombosed vessels. The system itself includes a console having an integrated computing system that itself includes a processing component and memory storing instructions executable by the processing component to enable the aspiration and lytic features of the AngioJet™ Thrombectomy System when in use with various peripherals (e.g., catheters, venous access devices, etc.). Medical devices with such processing features (e.g., AngioJet™ Thrombectomy System) may need to be updated after being deployed in the field. For example, a technician may need to update software, settings, or calibration parameters of the device. Such updating is often done in the field. Further, manufacturers often interrogate systems to access stored data related to performance metrics of the device.

Conventionally, accessing such "field service" features of a medical device is done with a simple username and password authentication scheme. However, this provides for limited security as the username and password combination must be set at the time the medical device is configured at the factory. As such, if the identities or roles of a field service technician changes after the device has been deployed, the username and password combinations stored in the medical device may no longer be valid.

Thus, there is a need for a more secure and flexible authentication scheme for medical devices to be updated in the field.

BRIEF SUMMARY

The present disclosure provides a secure authentication scheme for a field service technician to access a device (e.g., a medical device, or the like) in the field. The present disclosure can be provided for a field service technician to access system controls and data that a regular user (e.g., physician, clinical user, etc.) should not have access to.

Some embodiments of the disclosure can be implemented as a computer implemented method for a medical device. The computer implemented method can comprise determining, at a processor of a medical device, whether a credential package stored on a removable authentication device is authentic, wherein the removable authentication device is coupled to the medical device and wherein the medical device comprises the processor and a memory comprising instructions, which when executed by the processor cause the medical device to execute either a user application or a field service technician application; generating a first graphical indication that the credential package is not authentic and causing the first graphical indication to be displayed on a display coupled to the medical device based on a determination that credential package is not authentic; or verifying, at the processor based on a determination that the credential package is authentic, whether a field service technician attempting to access the medical device is authorized based on the credential package; and generating a second graphical indication that the field service technician is not authorized and causing the second graphical indication to be displayed on the display based on a determination that field service technician is not authorized; or executing the field service technician application based on a determination that field service technician is authorized.

In further embodiments, the computer implemented method can comprise determining, at the processor, whether the authentication device is coupled to the medical device; and determining, at the processor, whether the credential package is stored on the removable authentication device based on a determination that the authentication device is coupled to the medical device.

In further embodiments, the computer implemented method can comprise determining, at the processor, whether the authentication device is coupled to the medical device responsive to a trigger, wherein the trigger is a power cycle of the medical device, a power up of the medical device, or an input received from an input device of the medical device.

In further embodiments, the computer implemented method can comprise determining, at the processor, whether the credential package is authentic based on a determination that the credential package is stored on the removable authentication device.

In further embodiments, the computer implemented method can comprise verifying, at the processor based on a determination that the field service technician is authorized, whether the field service technician has a proper role to access the field service technician application; and generating a third graphical indication that the field service technician does not have the proper role and causing the third graphical indication to be displayed on the display based on a determination that field service technician does not have the proper role; or executing the field service technician application based on the determination that field service technician is authorized and a determination that the field service technician has the proper role.

In further embodiments, the computer implemented method can comprise identifying, at the processor based on a determination that the field service technician is authorized, a role of the field service technician; and executing a one of a plurality of field service technician applications based on the identified role of the field service technician.

In further embodiments of the computer implemented method, the role of the field service technician is one of a maintenance user role, a developer user role, or a manufacturing user role.

In further embodiments of the computer implemented method, the plurality of field service technician applications comprises a maintenance user application, a developer user application, and a manufacturing user application.

In further embodiments, the computer implemented method can comprise verifying, at the processor based on a determination that the field service technician is authorized, whether the field service technician has a proper training to access the field service technician application; and generating a third graphical indication that the field service technician does not have the proper training and causing the third graphical indication to be displayed on the display based on a determination that field service technician does not have the proper training; or executing the field service technician application based on the determination that field service technician is authorized and a determination that the field service technician has the proper training.

In further embodiments of the computer implemented method, the credential package is signed by a private key from an asymmetric key pair, and wherein determining, at the processor, whether the credential package is authentic comprising verifying the authenticity of the credential package using a public key from the asymmetric key pair.

In further embodiments of the computer implemented method, the credential package is encrypted by a public key from an asymmetric key pair, and wherein determining, at the processor, whether the credential package is authentic comprises decrypting the credential package using a private key from the asymmetric key pair.

In further embodiments of the computer implemented method, the memory comprises operating system (OS) instructions, which when executed by the processor cause the medical device to execute the OS, wherein the OS comprises a secure shell (SSH) and wherein verifying, at the processor, whether the field service technician is authorized comprises receiving at least a password from the field service technician; and establishing an SSH connection to the OS based in part on the password.

In further embodiments, the computer implemented method can comprise determining that the field service technician is authorized based on whether the SSH connection to the OS is successful.

Some embodiments of the disclosure can be implemented as an apparatus for a medical device. The apparatus can comprise a processor; and memory coupled to the processor, the memory comprising instructions, which when executed by the processor cause the processor to implement the method of any of the embodiments disclosed herein.

Some embodiments of the disclosure can be implemented as a computer-readable storage device comprising instruction, which when executed by a processor of a medical device cause the medical device to implement the method of any of the embodiments disclosed herein.

BRIEF SUMMARY OF THE DRAWINGS

To easily identify the discussion of any element or act, the most significant digit or digits in a reference number refer to the figure number in which that element is first introduced.

FIG. 5 illustrates another logic flow in accordance with at least one embodiment of the present disclosure.

FIG. 6 illustrates a computer-readable storage medium in accordance with at least one embodiment of the present disclosure.

DETAILED DESCRIPTION

Figure 1:
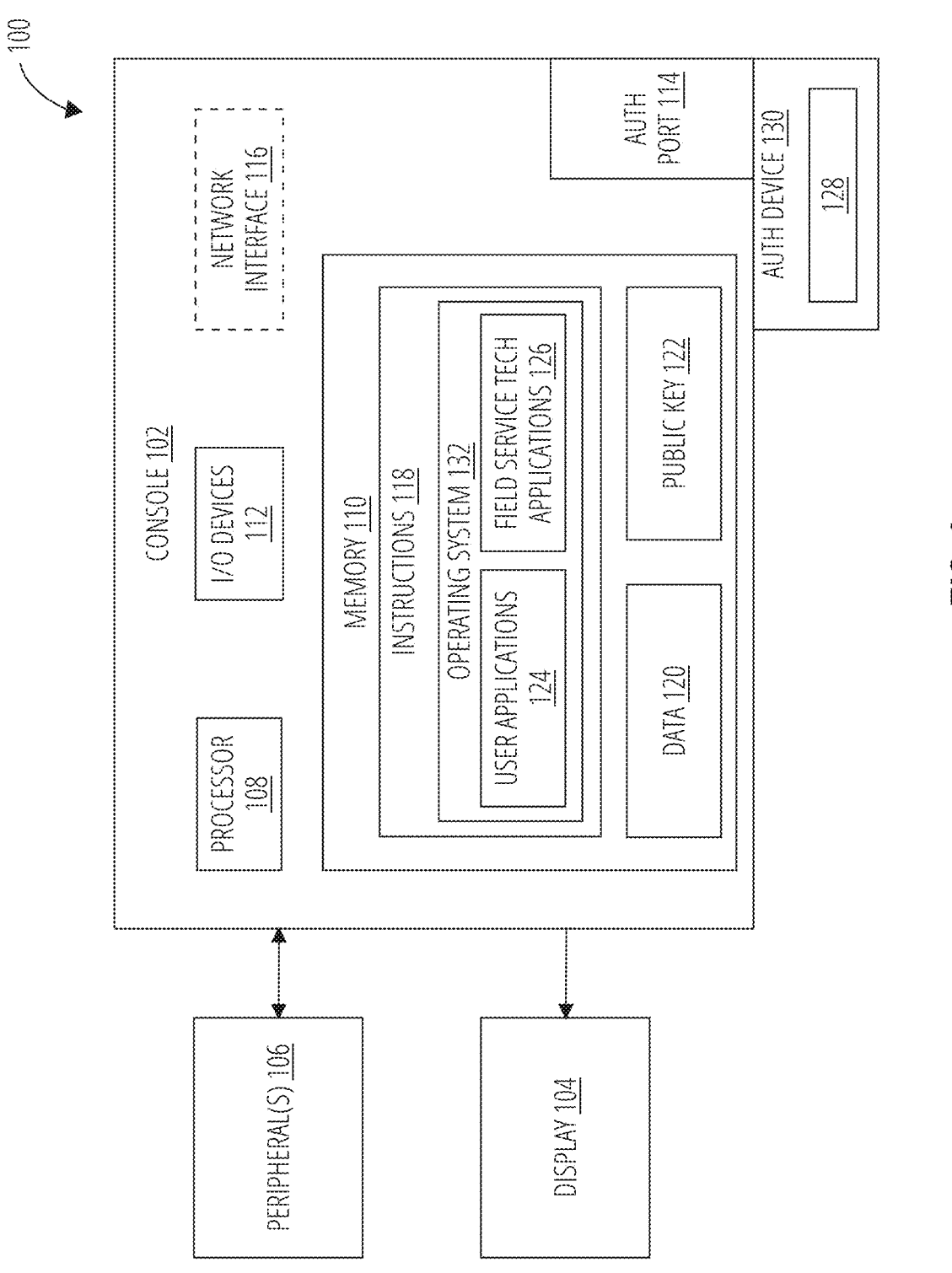
FIG. 1 illustrates medical device system in accordance with at least one embodiment of the present disclosure.

As noted, the present disclosure provides a secure authentication system for a field service technician to access system controls and data that a regular user does not have access to. FIG. 1 illustrates an example medical device system 100, in accordance with non-limiting example(s) of the present disclosure. In general, medical device system 100 can be any system (e.g., console, or the like) for a medical device. As a specific example, medical device system 100 can be the AngioJet™ Thrombectomy System. Medical device system 100 includes a console 102 and display 104. Optionally, medical device system 100 includes peripheral(s) 106 (e.g., catheters, access devices, sensors, etc.) useful in performing procedures with the medical device system 100.

Console 102 includes a housing as well as several computing devices components. In some embodiments, console 102 can be incorporated into and/or implemented by a housing that also contains display 104. With some embodiments, console 102 can be a workstation or server communicatively coupled to peripheral(s) 106 and/or display 104. Console 102 can include processor 108, memory 110, input and/or output (I/O) devices 112, and authentication port 114. Further, in some examples, medical device system 100 can optionally include network interface 116. However, it is to be appreciated that many medical devices (e.g., medical device system 100) are not provided with a network interface for purposes of physically securing the device against malicious actors.

The processor 108 may include circuitry or processor logic, such as, for example, any of a variety of commercial processors. In some examples, processor 108 may include multiple processors, a multi-threaded processor, a multi-core processor (whether the multiple cores coexist on the same or separate dies), and/or a multi-processor architecture of some other variety by which multiple physically separate processors are in some way linked. Additionally, in some examples, the processor 108 may include graphics processing portions and may include dedicated memory, multiple-threaded processing and/or some other parallel processing capability. In some examples, the processor 108 may be an application specific integrated circuit (ASIC) or a field programmable integrated circuit (FPGA).

The memory 110 may include logic, a portion of which includes arrays of integrated circuits, forming non-volatile memory to persistently store data or a combination of non-volatile memory and volatile memory. It is to be appreciated, that the memory 110 may be based on any of a variety of technologies. In particular, the arrays of integrated circuits included in memory 120 may be arranged to form one or more types of memory, such as, for example, dynamic random access memory (DRAM), NAND memory, NOR memory, or the like.

I/O devices 112 can be any of a variety of devices to receive input and/or provide output. For example, I/O devices 112 can include, a keyboard, a mouse, a joystick, a foot pedal, a display, a touch enabled display, a haptic feedback device, an LED, or the like.

Authentication port 114 can include any of a variety of ports or data access interfaces. For example, authentication port 114 can be a universal serial bus (USB) port. Network interface 116 can include logic and/or features to support a communication interface. For example, network interface 116 may include one or more interfaces that operate according to various communication protocols or standards to communicate over direct or network communication links. Direct communications may occur via use of communication protocols or standards described in one or more industry standards (including progenies and variants). For example, network interface 116 may facilitate communication over a bus, such as, for example, peripheral component interconnect express (PCIe), non-volatile memory express (NVMe), system management bus (SMBus), SAS (e.g., serial attached small computer system interface (SCSI)) interfaces, serial AT attachment (SATA) interfaces, or the like. Additionally, network interface 116 can include logic and/or features to enable communication over a variety of wired or wireless network standards (e.g., 802.11 communication standards). For example, network interface 116 may be arranged to support wired communication protocols or standards, such as, Ethernet, or the like. As another example, network interface 116 may be arranged to support wireless communication protocols or standards, such as, for example, Wi-Fi, Bluetooth, ZigBee, LTE, 5G, or the like.

Memory 110 can include instructions 118, data 120 and public key 122. Instructions 118 can itself includes user applications 124 and field service tech applications 126. It is noted that user applications 124 and field service tech applications 126 can be part of operating system (OS) 132. In some examples, OS 132 can be a Unix based operating system (e.g., a Linux distribution, or the like), Microsoft RT, or another operating system. During operation, processor 108 can execute instructions 118 to cause console 102 to perform a medical device procedure. For example, where the medical device system 100 is the AngioJet™ Thrombectomy System, processor 108 can execute instructions 118 to provide user applications 124 with which a physician can perform a thrombectomy procedure using peripheral(s) 106. During the thrombectomy procedure, the user can access user applications 124 to select (e.g., via input and/or output (I/O) devices 112) settings for the thrombectomy procedure. For example, user applications 124 can provide a graphical user interface (GUI) to be displayed on display 104 and with which a user can select parameters or settings for a procedure. Further, during the procedure, processor 108 can execute instructions 118 to receive information (e.g., user specified settings, sensed data, control signals, etc.) and store the information at data 120.

Additionally, processor 108 can execute instructions 118 to provide field service tech applications 126 responsive to a field service technician authenticating to the medical device system 100. In general, processor 108 can execute instructions 118 to authenticate a field service technician through a secure shell (e.g., SSH, or the like) using a cryptographic key (e.g., asymmetric cryptography, public key cryptography, or the like).

Prior to authenticating to the medical device system 100, the field service technician generates (e.g., at a computing device at the manufacturer, or the like) a credential package 128 and stores the credential package 128 on an authentication device 130. The credential package 128 can include a signed SSH credential package including, where the SSH credential package has been signed by a cryptographic key of a cryptographic key pair. This is explained in greater detail with respect to FIG. 2.

It is noted that although the medical device system 100 of FIG. 1 depicts public key 122 stored in memory 110 of medical device system 100, medical device system 100 could instead be arranged to store a private key from an asymmetric key pair. This will be described in greater detail below.

Figure 2:
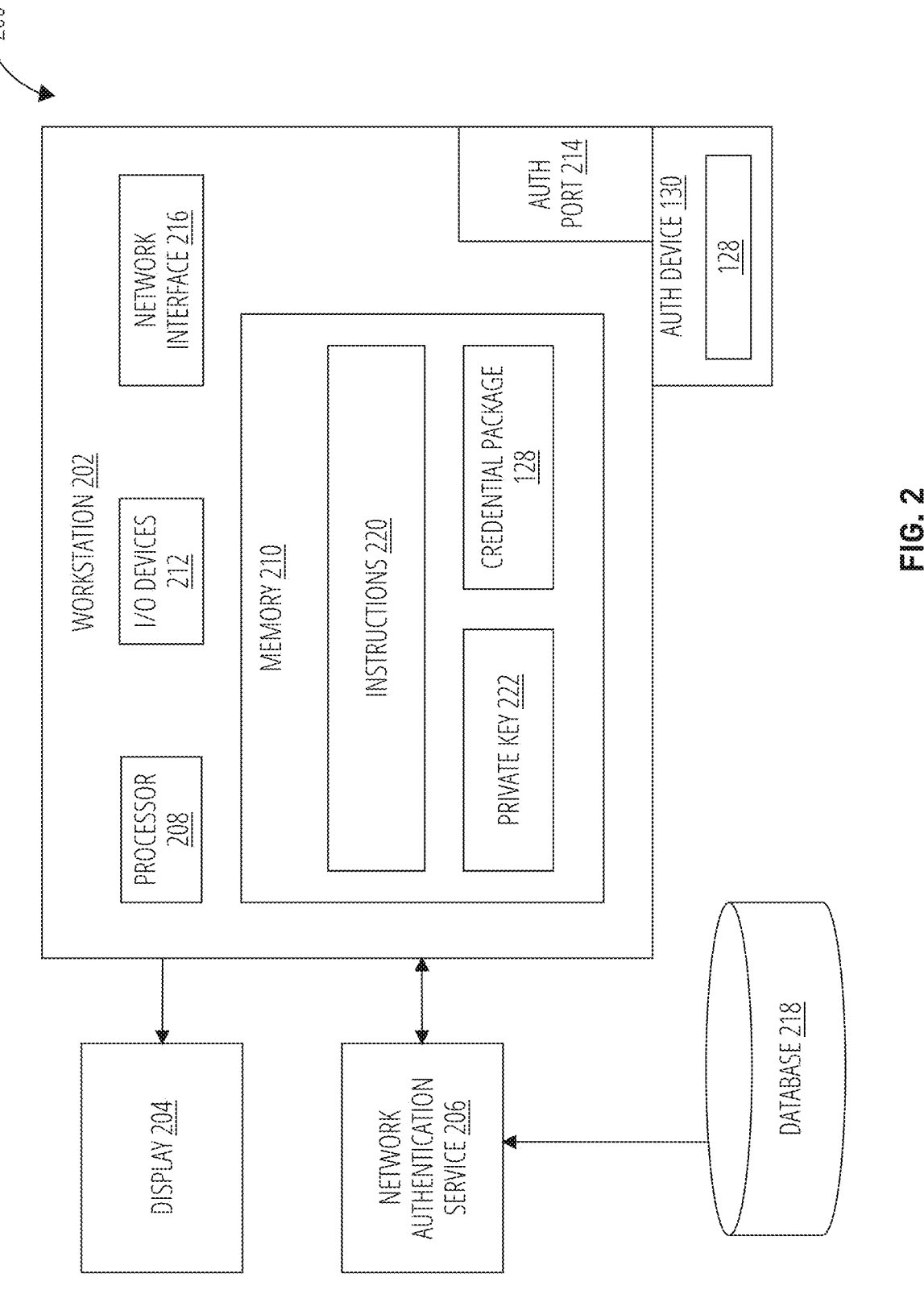
FIG. 2 illustrates credential generation system in accordance with at least one embodiment of the present disclosure.

FIG. 2 illustrates a credential generation system 200 including a workstation 202, with which a field service technician can generate credential package 128 as introduced above. Workstation 202 can be any of a variety of computing devices, such as, for example, a laptop computer, a tablet computer, a desktop computer, or the like. Workstation 202 can be coupled to or can incorporate (e.g., in the same housing, or the like) a display 204. Workstation 202 can include processor 208, memory 210, input and/or output (I/O) devices 212, authentication port 214, and network interface 216. Further, workstation 202 can be coupled to database 218. In general, database 218 can include (e.g., store) indications of field service technician credentials. This is described in greater detail below.

The processor 208 may include circuitry or processor logic, such as, for example, any of a variety of commercial processors. In some examples, processor 208 may include multiple processors, a multi-threaded processor, a multi-core processor (whether the multiple cores coexist on the same or separate dies), and/or a multi-processor architecture of some other variety by which multiple physically separate processors are in some way linked. Additionally, in some examples, the processor 208 may include graphics processing portions and may include dedicated memory, multiple-threaded processing and/or some other parallel processing capability. In some examples, the processor 208 may be an application specific integrated circuit (ASIC) or a field programmable integrated circuit (FPGA).

The memory 210 may include logic, a portion of which includes arrays of integrated circuits, forming non-volatile memory to persistently store data or a combination of non-volatile memory and volatile memory. It is to be appreciated, that the memory 210 may be based on any of a variety of technologies. In particular, the arrays of integrated circuits included in memory 120 may be arranged to form one or more types of memory, such as, for example, dynamic random access memory (DRAM), NAND memory, NOR memory, or the like.

I/O devices 212 can be any of a variety of devices to receive input and/or provide output. For example, I/O devices 212 can include, a keyboard, a mouse, a joystick, a foot pedal, a display, a touch enabled display, a haptic feedback device, an LED, or the like.

Authentication port 214 can include any of a variety of ports or data access interfaces. For example, authentication port 214 can be a universal serial bus (USB) port. Network interface 216 can include logic and/or features to support a communication interface. For example, network interface 216 may include one or more interfaces that operate according to various communication protocols or standards to communicate over direct or network communication links. Direct communications may occur via use of communication protocols or standards described in one or more industry standards (including progenies and variants). For example, network interface 216 may facilitate communication over a bus, such as, for example, peripheral component interconnect express (PCIe), non-volatile memory express (NVMe), system management bus (SMBus), SAS (e.g., serial attached small computer system interface (SCSI)) interfaces, serial AT attachment (SATA) interfaces, or the like. Additionally, network interface 216 can include logic and/or features to enable communication over a variety of wired or wireless network standards (e.g., 802.11 communication standards). For example, network interface 216 may be arranged to support wired communication protocols or standards, such as, Ethernet, or the like. As another example, network interface 216 may be arranged to support wireless communication protocols or standards, such as, for example, Wi-Fi, Bluetooth, ZigBee, LTE, 5G, or the like.

Memory 210 can include instructions 220, private key 222, and credential package 128. During operation, processor 208 can execute instructions 220 to cause workstation 202 to generate credential package 128 and store credential package 128 on authentication device 130 via authentication port 114. Subsequently, the field service technician can use the credential package 128 and authentication device 130 to access field service tech applications 126 as outlined above and described with reference to FIG. 1.

In an illustrative example, processor 108 can execute instructions 118 to authenticate a user to network authentication service 206. In general, network authentication service 206 can be a corporate network or secure local area network with which a user must provide credentials (e.g., username and password combination, two factor authentication code, or the like) to access. Responsive to authenticating the field service technician to the network authentication service 206, processor 208 can execute instructions 220 to generate an SSH credential package and sign the package using private key 222 of the cryptographic key pair that includes both private key 222 and public key 122. In general, the credential package 128 can be an indication of an authorized field service technician and username/password combination with which the field service technician can authenticate with. Further, in some embodiments, the credential package 128 can include an indication of a role of the field service technician and/or training or certification levels of the field service technician. This is explained in greater detail below.

With some examples, the signed SSH credential package can be password protected. In further examples, processor 208 can execute instructions 220 to receive the password from the field service technician (e.g., via input and/or output (I/O) devices 212, or the like) and can secure the credential package 128 with the received password. Further, in some embodiments, processor 208 can execute instructions 220 to receive an indication from the field service technician (e.g., via input and/or output (I/O) devices 212, or the like) of a time limit (e.g., 1 day, 1 week, 1 month, etc.) at the expiration of which, credential package 128 will expire.

As noted, although the credential generation system 200 of FIG. 2 depicts private key 222 stored in memory 210 of credential generation system 200, credential generation system 200 could be arranged to store public key 122 key from the asymmetric key pair instead. This will be described in greater detail below.

Figure 3:
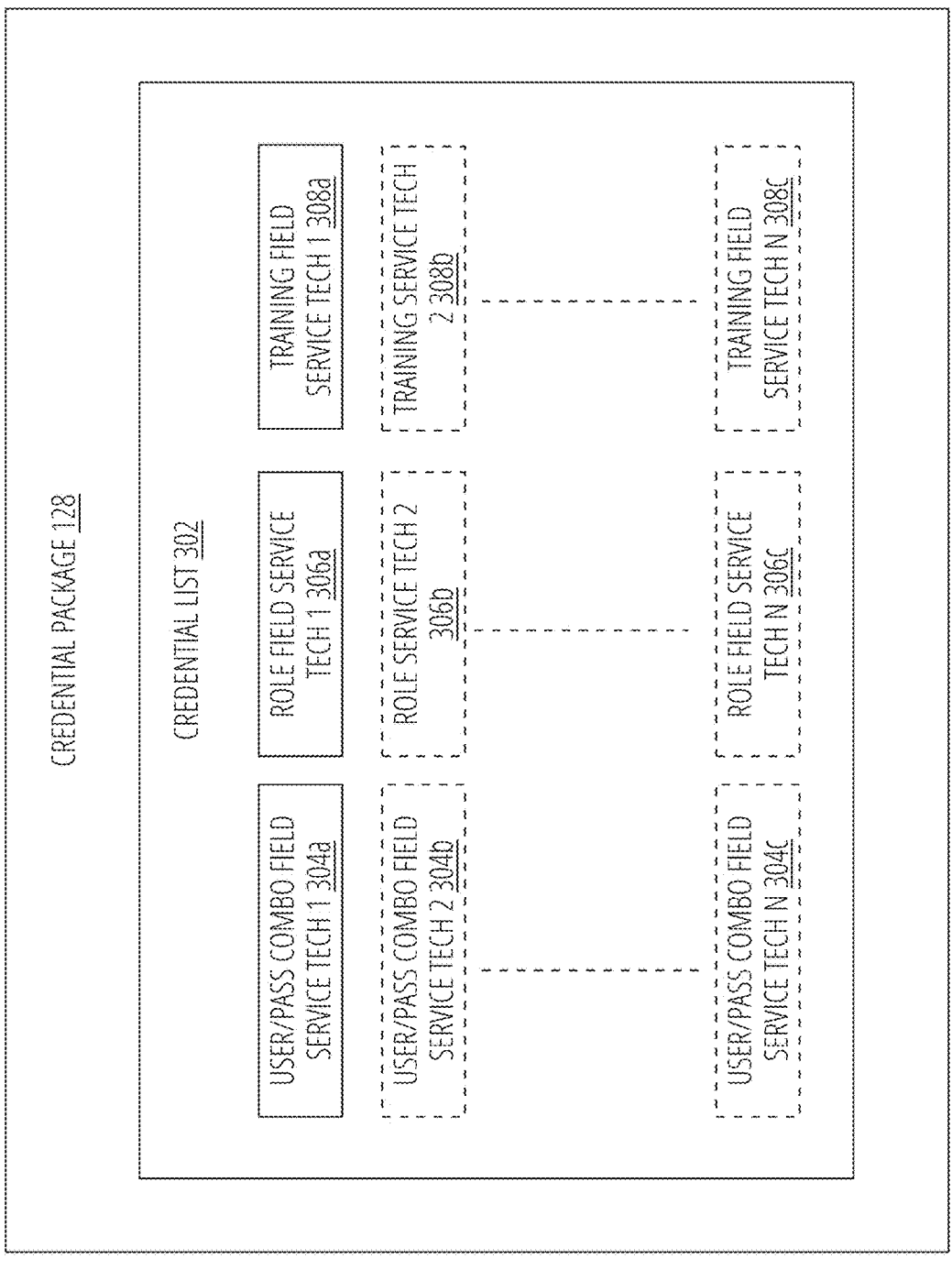
FIG. 3 illustrates an aspect of the subject matter in accordance with at least one embodiment of the present disclosure.

FIG. 3 illustrates an example of credential package 128, which can be stored on a computer-readable medium or computer-readable storage device, such as, authentication device 130. In some embodiments, credential package 128 can include a credential list 302 listing indications for one or more field service technicians. In a simple example, each field service technician can create their own credential package 128 and store it on an individual (e.g., corporate issued, or the like) authentication device 130. However, with some embodiments, a credential package 128 can include indications for multiple field service technicians. For example, FIG. 3 illustrates an example credential package 128 comprising credential list 302. Credential list 302 can be a data structure or information element comprising indications of username/password combination field service tech 1 304a, username/password combination field service tech 2 304b, and username/password combination field service tech N 304c. Further, in some embodiments, credential list 302 can also include indications of role field service tech 1 306a, role service tech 2 306b, and role field service tech N 306c and/or training field service tech 1 308a, training service tech 2 308b, and training field service tech N 308c.

Returning to FIG. 1, during operation, processor 108 can execute instructions 118 to provide field service tech applications 126 responsive to authenticating a field service technician to medical device system 100 as outlined above. For example, processor 108 can execute instructions 118 to verify the credential package 128 using public key 122 or the public key 122 and password combination with which the credential package 128 is secured. Further, processor 108 can execute instructions 118 to authenticate a particular field service technician (e.g., technician 1, technician 2, etc.) using the username/password combination field service tech 1 304a, 304b, or 304c and verify the field service technician accessing the medical device system 100 has a proper role and/or training (e.g., using 306a, 306b, 306c and/or 308a, 308b, and 308c).

In some embodiments, multiple different field service tech applications 126 can be provided and executed based on the role of the user. For example, a role of developer user, field service technician, or manufacturing user could be provided and processor 108 can execute instructions 118 to provide application 126 having functions associated with the role (e.g., field service technician, developer user, manufacturing user, etc.) of the user authenticating to the medical device system 100. Further, it is noted that although the term "field service technician" is used throughout this disclosure to identify a user attempting to authenticate to the medical device system 100 and access the field service tech application 126, this is not intended to be limiting and the user could be instead a maintenance user, developer user, a manufacturer user, or other type of user. As such, the term "field service technician" can be used interchangeably with the term "field user" or "field service user" and can include multiple types of users.

Figure 4:
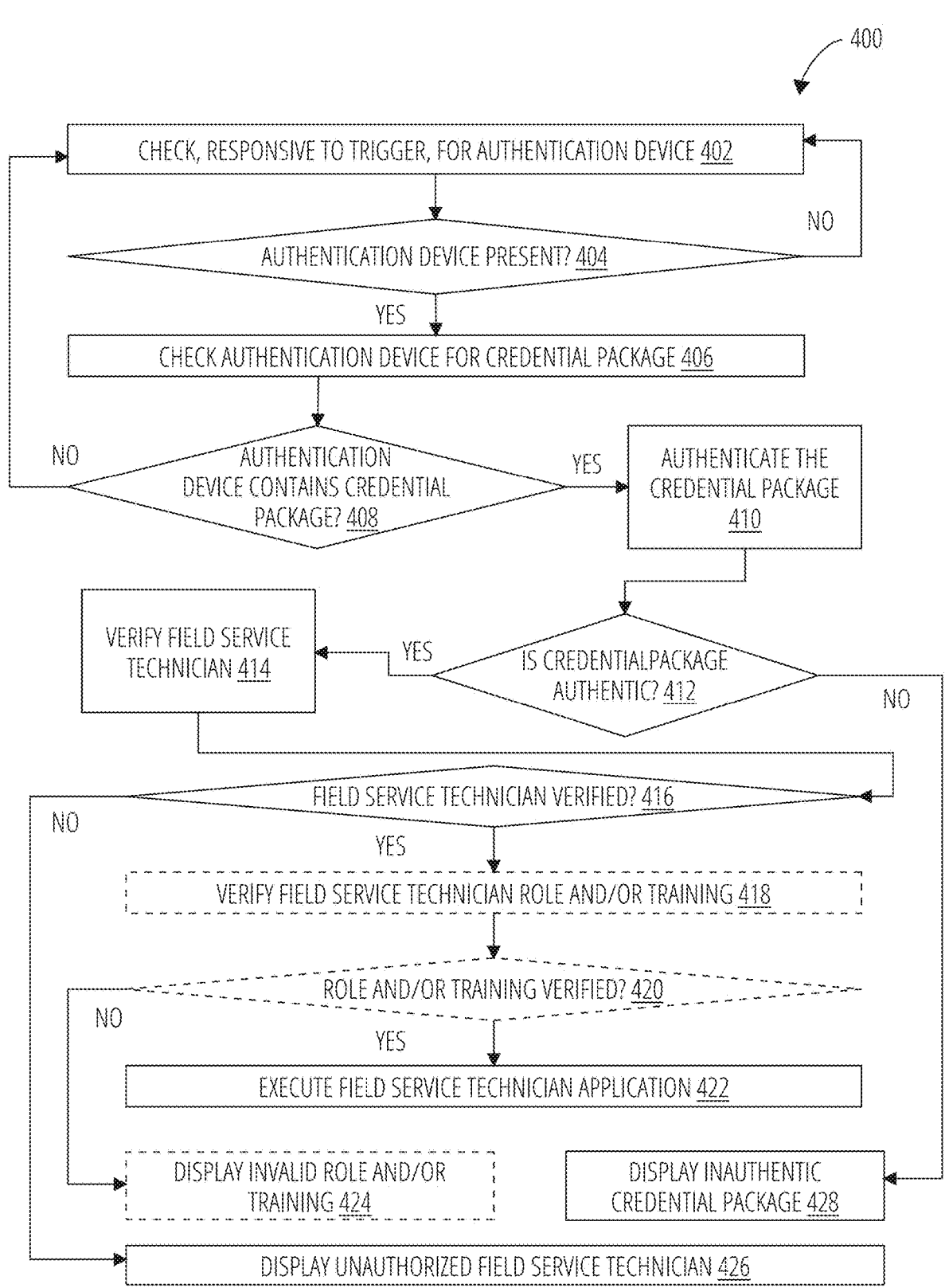
FIG. 4 illustrates a logic flow in accordance with at least one embodiment of the present disclosure.

FIG. 4 illustrates a method 400, which may be implemented in accordance with embodiments of the present disclosure. It is noted that method 400 is described with reference to the medical device system 100 of FIG. 1. However, this is for purposes of clarity of presentation only and it will be appreciated that method 400 could be practiced with a system different from the medical device system 100.

Method 400 can begin at block 402. At block 402 "check, responsive to trigger, for authentication device" a computing system checks for the presence of an authentication device, often in response to a trigger. For example, medical device system 100 can check for the presence of authentication device 130 responsive to a trigger (e.g., startup, restart, user log out, etc.) Specifically, processor 108 can execute instructions 118 to detect whether authentication device 130 is electrically coupled to authentication port 114.

Continuing to decision block 404 "authentication device present?" a determination is made as to whether the authentication device is present. For example, processor 108 can execute instructions 118 to determine whether the authentication device 130 was detected at block 402. From decision block 404, method 400 can continue to either block 406 or return to block 402. Specifically, method 400 can continue from decision block 404 to block 406 based on a determination at decision block 404 that the authentication device is present while method 400 can return to block 402 based on a determination at decision block 404 that the authentication device is not present.

At block 406 "check authentication device for credential package" the authentication device is checked (or searched) for a credential package. For example, processor 108 can execute instructions 118 to search authentication device 130 for credential package 128. Continuing to decision block 408 "authentication device contains credential package?" a determination is made as to whether the authentication device contains a credential package. For example, processor 108 can execute instructions 118 to determine whether the authentication device 130 includes or contains credential package 128. From decision block 408, method 400 can continue to either block 410 or return to block 402. Specifically, method 400 can continue from decision block 408 to block 410 based on a determination at decision block 408 that the authentication device contains a credential package while method 400 can return to block 402 based on a determination at decision block 408 that the authentication device does not contain a credential package.

At block 410 "authenticate the credential package" the credential package is authenticated. For example, processor 108 can execute instructions 118 to decrypt or authenticate the credential package 128 with the public key 122. As outlined above, the credential package 128 is initially secured with the private key 222 at the time the credential package 128 is generated. As such, during use, the credential package 128 can be authenticated with the public key 122, where the public key 122 and private key 222 are a public/private key pair. With some examples, the credential package 128 can be signed by a private key from an asymmetric key pair (e.g., private key 222) and can then be authenticated (e.g., verified using public key 122 and an asymmetric key verification algorithm, or the like). In other examples, the credential package 128 can be encrypted by a public key from an asymmetric key pair (e.g., public key 122) and can then be authenticated (e.g., verified using private key 222 and an asymmetric key decryption algorithm, or the like).

Continuing to decision block 412 "is credential package authentic?" a determination is made as to whether the credential package is authentic. For example, processor 108 can execute instructions 118 to determine whether the credential package 128 is authentic (e.g., verifiable based on public key 122, or the like). From decision block 412, method 400 can continue to either block 414 or block 428. Specifically, method 400 can continue from decision block 412 to block 414 based on a determination at decision block 412 that the credential package is authentic while method 400 can continue from decision block 412 to block 428 based on a determination at decision block 412 that the credential package is not authentic.

At block 414 "verify field service technician" the field service technician interacting with the system is verified. For example, processor 108 can execute instructions 118 to verify the field service technician attempting to unlock the field service tech applications 126 of the medical device system 100. Specifically, responsive to authenticating processor 108 can execute instructions 118 to request a username and/or password combination from the user (e.g., presumably a field service technician, or the like) interacting with the medical device system 100. Processor 108 can execute instructions 118 to receive input, responsive to the request, corresponding to a username and/or password combination and can establish a local connection to the OS 132 via an SSH connection, or the like. In some embodiments, the OS 132 can be configured to use the credential list 302 (e.g., username/password combination field service tech 1 304*a*, username/password combination field service tech 2 304*b*, username/password combination field service tech N 304*c*, etc.) to authenticate the user credentials received at block 414 and establish the local connection to OS 132 via SSH.

Continuing to decision block 416 "field service technician verified?" a determination is made as to whether the field service technician is verified. For example, processor 108 can execute instructions 118 to determine whether the user (e.g., field service technician, or the like) is verified, or could establish a local connection to the OS 132 (e.g., via SSH, or the like). From decision block 416, method 400 can continue to either block 418 (where provided, or block 422 where optional block 418 is not provided) or block 426. Specifically, method 400 can continue from decision block 416 to block 418 (or 422 as outlined below) based on a determination at decision block 416 that the field service technician is verified while method 400 can continue from decision block 416 to block 426 based on a determination at decision block 416 that the field service technician is not verified (e.g., the local connection to the OS 132 is not established).

With some embodiments, method 400 can optionally include block 418 and decision block 420. As noted, where method 400 includes block 418 and decision block 420, method 400 can continue from decision block 416 to block 418 based on a determination that the field service technician is verified. At block 418 "verify field service technician role and/or training" the role and/or training of the field service technician verified at block 414 and decision block 416 can be verified. For example, processor 108 can execute instructions 118 to verify the role and/or training of the field service technician based on credential list 302. As a specific example, processor 108 can execute instructions 118 to check whether the user that established a local connection to the OS 132 has the correct role based on role field service tech 1 306*a*, role service tech 2 306*b*, role field service tech N 306*c*, etc. and/or the correct training based on training field service tech 1 308*a*, training service tech 2 308*b*, training field service tech N 308*c*, etc.

From block 418, method 400 can continue to decision block 420. At decision block 420 "role and/or training verified?" a determination is made as to whether the field service technician has the correct role and/or training. For example, processor 108 can execute instructions 118 to determine whether the user (e.g., field service technician, or the like) has the correct role and/or training to access field service tech applications 126. From decision block 420, method 400 can continue to either block 422 or block 424. Specifically, method 400 can continue from decision block 420 to block 422 based on a determination at decision block 418 that the field service technician has the proper role and/or training while method 400 can continue from decision block 418 to block 424 based on a determination at decision block 418 that the field service technician does not have the proper role and/or training.

At block 422 "execute field service technician application" the field service technician application can be executed. For example, processor 108 can execute instructions 118 to cause field service tech applications 126 to be executed and/or provided by OS 132. As noted above, with some embodiments, field service tech applications 126 can be configured to provide an alternative graphical user interface with access to settings, information, data (e.g., data 120) and software update features (e.g., to update instructions 118, OS 132, user applications 124, field service tech applications 126, or the like) not provided or accessible via user applications 124 (e.g., during normal operation of the medical device system 100).

At block 424 "display invalid role and/or training" an indication that the role and/or training is invalid can be displayed. For example, processor 108 can execute instructions 118 to cause a graphical indication (e.g., text box, image, or the like) to be displayed on display 104 indicating that the field service technician does not have the proper role and/or training to access field service tech applications 126.

At block 426 "display unauthorized field service technician" an indication that the field service technician is unauthorized can be displayed. For example, processor 108 can execute instructions 118 to cause a graphical indication (e.g., text box, image, or the like) to be displayed on display 104 indicating that the field service technician is not authorized to access field service tech applications 126.

At block 428 "display inauthentic credential package" an indication that the credential package is not authentic can be displayed. For example, processor 108 can execute instructions 118 to cause a graphical indication (e.g., text box, image, or the like) to be displayed on display 104 indicating that the credential package 128 is not authentic.

FIG. 5 illustrates a method 500 for generating a credential package 128 according to some embodiments of the present disclosure. It is noted that method 500 is described with reference to the credential generation system 200 of FIG. 2. However, this is for purposes of clarity of presentation only and it will be appreciated that method 500 could be practiced with a system different from the credential generation system 200.

Method 500 can begin at block 502. At block 502 "receive request to generate credential package" a request to generate a credential package can be received by a computing system. For example, in executing instructions 220, processor 208 can receive (e.g., from input and/or output (I/O) devices 212, or the like) a request from a user to generate credential package 128. Continuing to block 504 "receive username and password for field service technician" the username and password for the field service technician requesting the credential package can be received. For example, processor 208 can execute instructions 220 to receive an indication of the username and password for the field service technician requesting the credential package 128.

Continuing to block 506 "access list of current field service technicians" a list of current field service technicians can be accessed. For example, processor 208 can execute instructions 220 to access a listing of current field service technicians and their roles and/or training from database 218. Continuing to block 508 "generate credential list including at least field service technician" a credential list including an indication of at least the field service technician requesting the credential package can be generated. For example, processor 208 can execute instructions 220 to generate a data structure or information element like credential list 302 comprising indications of at least 304a and optionally 304b and 304c. Further, the credential list 302 can optionally include 306a, 306b, 306c and/or 308a, 308b, and 308c.

Continuing to block 510 "sign the credential list with a private key from a public/private key pair" the credential list can be encrypted with a private key from a public private key pair. For example, processor 208 can execute instructions 220 to sign the credential list 302 with the private key 222 to from credential package 128. In some embodiments, the credential package 128 can be a zip file comprising text files associated with the field service technicians' usernames and passwords, roles, and training, which is encrypted with a public key (e.g., public key 122) from the asymmetric key pair.

Continuing to block 512 "store the encrypted credential list on a removable storage device" the encrypted credential list can be stored on a removable storage device. For example, processor 208 can execute instructions 220 to store (e.g., write the file to) the credential package 128 to authentication device 130.

FIG. 6 illustrates computer-readable storage medium 600. Computer-readable storage medium 600 may comprise any non-transitory computer-readable storage medium or machine-readable storage medium, such as an optical, magnetic or semiconductor storage medium. In various embodiments, computer-readable storage medium 600 may comprise an article of manufacture. In some embodiments, 700 may store computer executable instructions 602 with which circuitry (e.g., processor 108, processor 208, or the like) can execute. For example, computer executable instructions 602 can include instructions to implement operations described with respect to method 400 and/or method. Examples of computer-readable storage medium 600 or machine-readable storage medium may include any tangible media capable of storing electronic data, including volatile memory or non-volatile memory, removable or non-removable memory, erasable or non-erasable memory, writeable or re-writeable memory, and so forth. Examples of computer executable instructions 602 may include any suitable type of code, such as source code, compiled code, interpreted code, executable code, static code, dynamic code, object-oriented code, visual code, and the like.

Figure 7:
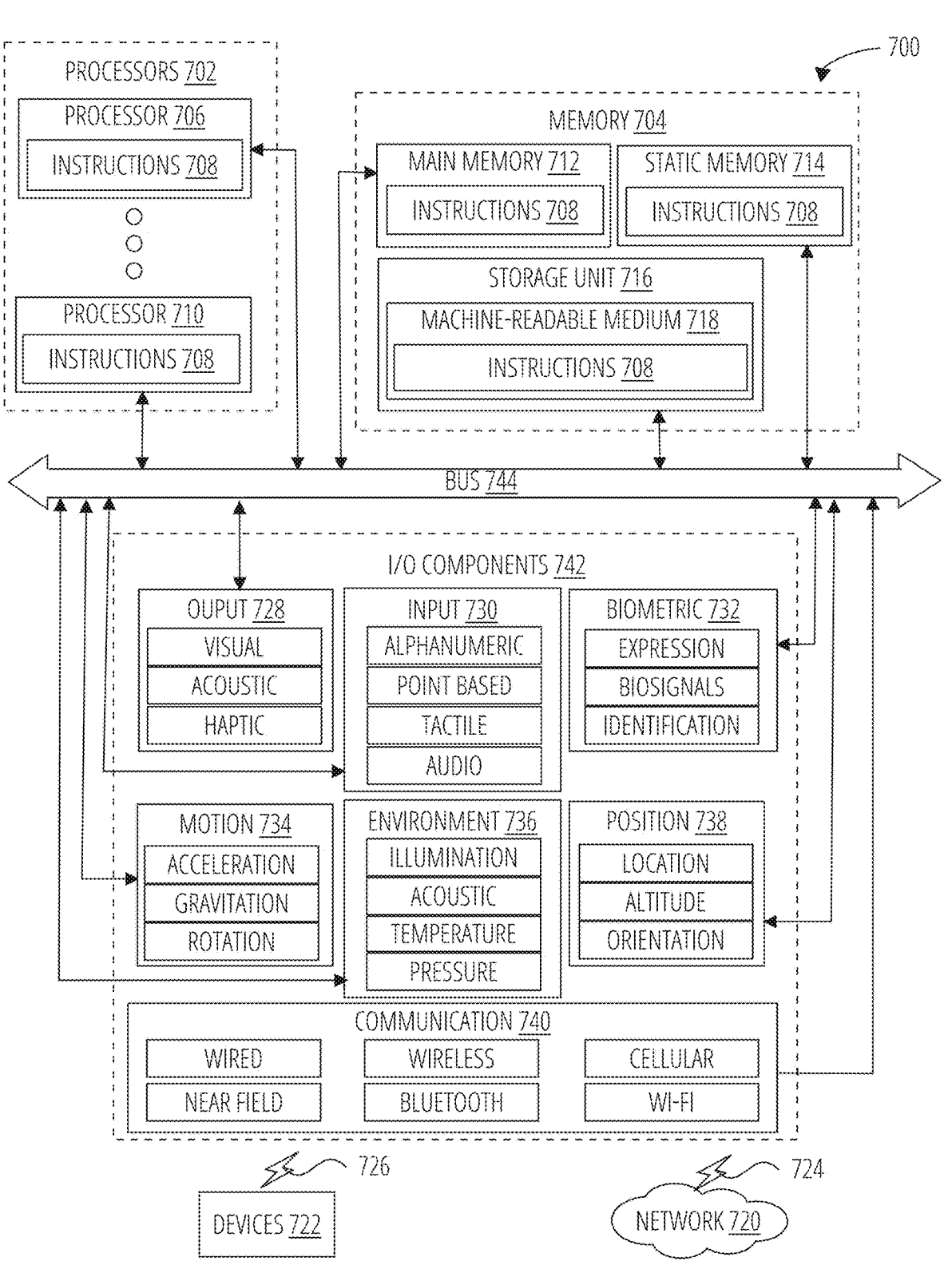
FIG. 7 illustrates a diagrammatic representation of a machine in the form of a computer system within which a set of instructions may be executed for causing the machine to perform any one or more of the methodologies discussed herein, in accordance with at least one embodiment of the present disclosure.

FIG. 7 illustrates a diagrammatic representation of a machine 700 in the form of a computer system within which a set of instructions may be executed for causing the machine to perform any one or more of the methodologies discussed herein. More specifically, FIG. 7 shows a diagrammatic representation of the machine 700 in the example form of a computer system, within which instructions 708 (e.g., software, a program, an application, an applet, an app, or other executable code) for causing the machine 700 to perform any one or more of the methodologies discussed herein may be executed. For example, the instructions 708 may cause the machine 700 to execute instructions 118 of FIG. 1, instructions 220 of FIG. 2, method 400 of FIG. 4, method 500 or FIG. 5, or the like. More generally, the instructions 708 may cause the machine 700 to unlock and/or authenticate a user to a separate field service application as outlined herein or to generate an encrypted credential list with which the field service application can be unlocked.

The instructions 708 transform the general, non-programmed machine 700 into a particular machine 700 programmed to carry out the described and illustrated functions in a specific manner. In alternative embodiments, the machine 700 operates as a standalone device or may be coupled (e.g., networked) to other machines. In a networked deployment, the machine 700 may operate in the capacity of a server machine or a client machine in a server-client network environment, or as a peer machine in a peer-to-peer (or distributed) network environment. The machine 700 may comprise, but not be limited to, a server computer, a client computer, a personal computer (PC), a tablet computer, a laptop computer, a netbook, a set-top box (STB), a PDA, an entertainment media system, a cellular telephone, a smart phone, a mobile device, a wearable device (e.g., a smart watch), a smart home device (e.g., a smart appliance), other smart devices, a web appliance, a network router, a network switch, a network bridge, or any machine capable of executing the instructions 708, sequentially or otherwise, that specify actions to be taken by the machine 700. Further, while only a single machine 700 is illustrated, the term "machine" shall also be taken to include a collection of machines 200 that individually or jointly execute the instructions 708 to perform any one or more of the methodologies discussed herein.

The machine 700 may include processors 702, memory 704, and I/O components 742, which may be configured to communicate with each other such as via a bus 744. In an example embodiment, the processors 702 (e.g., a Central Processing Unit (CPU), a Reduced Instruction Set Computing (RISC) processor, a Complex Instruction Set Computing (CISC) processor, a Graphics Processing Unit (GPU), a Digital Signal Processor (DSP), an ASIC, a Radio-Frequency Integrated Circuit (RFIC), another processor, or any suitable combination thereof) may include, for example, a processor 706 and a processor 710 that may execute the instructions 708. The term "processor" is intended to include multi-core processors that may comprise two or more independent processors (sometimes referred to as "cores") that may execute instructions contemporaneously. Although FIG. 7 shows multiple processors 702, the machine 700 may include a single processor with a single core, a single processor with multiple cores (e.g., a multi-core processor), multiple processors with a single core, multiple processors with multiples cores, or any combination thereof.

The memory 704 may include a main memory 712, a static memory 714, and a storage unit 716, both accessible to the processors 702 such as via the bus 744. The main memory 704, the static memory 714, and storage unit 716 store the instructions 708 embodying any one or more of the methodologies or functions described herein. The instructions 708 may also reside, completely or partially, within the main memory 712, within the static memory 714, within machine-readable medium 718 within the storage unit 716, within at least one of the processors 702 (e.g., within the processor's cache memory), or any suitable combination thereof, during execution thereof by the machine 700.

The I/O components 742 may include a wide variety of components to receive input, provide output, produce output, transmit information, exchange information, capture measurements, and so on. The specific I/O components 742 that are included in a particular machine will depend on the type of machine. For example, portable machines such as mobile phones will likely include a touch input device or other such input mechanisms, while a headless server machine will likely not include such a touch input device. It will be appreciated that the I/O components 742 may include many other components that are not shown in FIG. 7. The I/O components 742 are grouped according to functionality merely for simplifying the following discussion and the grouping is in no way limiting. In various example embodiments, the I/O components 742 may include output components 728 and input components 730. The output components 728 may include visual components (e.g., a display such as a plasma display panel (PDP), a light emitting diode (LED) display, a liquid crystal display (LCD), a projector, or a cathode ray tube (CRT)), acoustic components (e.g., speakers), haptic components (e.g., a vibratory motor, resistance mechanisms), other signal generators, and so forth. The input components 730 may include alphanumeric input components (e.g., a keyboard, a touch screen configured to receive alphanumeric input, a photo-optical keyboard, or other alphanumeric input components), point-based input components (e.g., a mouse, a touchpad, a trackball, a joystick, a motion sensor, or another pointing instrument), tactile input components (e.g., a physical button, a touch screen that provides location and/or force of touches or touch gestures, or other tactile input components), audio input components (e.g., a microphone), and the like.

In further example embodiments, the I/O components 742 may include biometric components 732, motion components 734, environmental components 736, or position components 738, among a wide array of other components. For example, the biometric components 732 may include components to detect expressions (e.g., hand expressions, facial expressions, vocal expressions, body gestures, or eye tracking), measure biosignals (e.g., blood pressure, heart rate, body temperature, perspiration, or brain waves), identify a person (e.g., voice identification, retinal identification, facial identification, fingerprint identification, or electroencephalogram-based identification), and the like. The motion components 734 may include acceleration sensor components (e.g., accelerometer), gravitation sensor components, rotation sensor components (e.g., gyroscope), and so forth. The environmental components 736 may include, for example, illumination sensor components (e.g., photometer), temperature sensor components (e.g., one or more thermometers that detect ambient temperature), humidity sensor components, pressure sensor components (e.g., barometer), acoustic sensor components (e.g., one or more microphones that detect background noise), proximity sensor components (e.g., infrared sensors that detect nearby objects), gas sensors (e.g., gas detection sensors to detection concentrations of hazardous gases for safety or to measure pollutants in the atmosphere), or other components that may provide indications, measurements, or signals corresponding to a surrounding physical environment. The position components 738 may include location sensor components (e.g., a GPS receiver component), altitude sensor components (e.g., altimeters or barometers that detect air pressure from which altitude may be derived), orientation sensor components (e.g., magnetometers), and the like.

Communication may be implemented using a wide variety of technologies. The I/O components 742 may include communication components 740 operable to couple the machine 700 to a network 720 or devices 722 via a coupling 724 and a coupling 726, respectively. For example, the communication components 740 may include a network interface component or another suitable device to interface with the network 720. In further examples, the communication components 740 may include wired communication components, wireless communication components, cellular communication components, Near Field Communication (NFC) components, Bluetooth® components (e.g., Bluetooth® Low Energy), Wi-Fi® components, and other communication components to provide communication via other modalities. The devices 722 may be another machine or any of a wide variety of peripheral devices (e.g., a peripheral device coupled via a USB).

Moreover, the communication components 740 may detect identifiers or include components operable to detect identifiers. For example, the communication components 740 may include Radio Frequency Identification (RFID) tag reader components, NFC smart tag detection components, optical reader components (e.g., an optical sensor to detect one-dimensional bar codes such as Universal Product Code (UPC) bar code, multi-dimensional bar codes such as Quick Response (QR) code, Aztec code, Data Matrix, Dataglyph, MaxiCode, PDF417, Ultra Code, UCC RSS-2D bar code, and other optical codes), or acoustic detection components (e.g., microphones to identify tagged audio signals). In addition, a variety of information may be derived via the communication components 740, such as location via Internet Protocol (IP) geolocation, location via Wi-Fi® signal triangulation, location via detecting an NFC beacon signal that may indicate a particular location, and so forth.

The various memories (i.e., memory 704, main memory 712, static memory 714, and/or memory of the processors 702) and/or storage unit 716 may store one or more sets of instructions and data structures (e.g., software) embodying or utilized by any one or more of the methodologies or functions described herein. These instructions (e.g., the instructions 708), when executed by processors 702, cause various operations to implement the disclosed embodiments.

As used herein, the terms "machine-storage medium," "device-storage medium," "computer-storage medium" mean the same thing and may be used interchangeably in this disclosure. The terms refer to a single or multiple storage devices and/or media (e.g., a centralized or distributed database, and/or associated caches and servers) that store executable instructions and/or data. The terms shall accordingly be taken to include, but not be limited to, solid-state memories, and optical and magnetic media, including memory internal or external to processors. Specific examples of machine-storage media, computer-storage media and/or device-storage media include non-volatile memory, including by way of example semiconductor memory devices, e.g., erasable programmable read-only memory (EPROM), electrically erasable programmable read-only memory (EEPROM), FPGA, and flash memory devices; magnetic disks such as internal hard disks and removable disks; magneto-optical disks; and CD-ROM and DVD-ROM disks. The terms "machine-storage media," "computer-storage media," and "device-storage media" specifically exclude carrier waves, modulated data signals, and other such media, at least some of which are covered under the term "signal medium" discussed below.

In various example embodiments, one or more portions of the network 720 may be an ad hoc network, an intranet, an extranet, a VPN, a LAN, a WLAN, a WAN, a WWAN, a MAN, the Internet, a portion of the Internet, a portion of the PSTN, a plain old telephone service (POTS) network, a cellular telephone network, a wireless network, a Wi-Fi® network, another type of network, or a combination of two or more such networks. For example, the network 720 or a portion of the network 720 may include a wireless or cellular network, and the coupling 724 may be a Code Division Multiple Access (CDMA) connection, a Global System for Mobile communications (GSM) connection, or another type of cellular or wireless coupling. In this example, the coupling 724 may implement any of a variety of types of data transfer technology, such as Single Carrier Radio Transmission Technology (1×RTT), Evolution-Data Optimized (EVDO) technology, General Packet Radio Service (GPRS) technology, Enhanced Data rates for GSM Evolution (EDGE) technology, third Generation Partnership Project (3GPP) including 3G, fourth generation wireless (4G) networks, Universal Mobile Telecommunications System (UMTS), High Speed Packet Access (HSPA), Worldwide Interoperability for Microwave Access (WiMAX), Long Term Evolution (LTE) standard, others defined by various standard-setting organizations, other long range protocols, or other data transfer technology.

The instructions 708 may be transmitted or received over the network 720 using a transmission medium via a network interface device (e.g., a network interface component included in the communication components 740) and utilizing any one of several well-known transfer protocols (e.g., hypertext transfer protocol (HTTP)). Similarly, the instructions 708 may be transmitted or received using a transmission medium via the coupling 726 (e.g., a peer-to-peer coupling) to the devices 722. The terms "transmission medium" and "signal medium" mean the same thing and may be used interchangeably in this disclosure. The terms "transmission medium" and "signal medium" shall be taken to include any intangible medium that can store, encoding, or carrying the instructions 708 for execution by the machine 700, and includes digital or analog communications signals or other intangible media to facilitate communication of such software. Hence, the terms "transmission medium" and "signal medium" shall be taken to include any form of modulated data signal, carrier wave, and so forth. The term "modulated data signal" means a signal that has one or more of its characteristics set or changed in such a matter as to encode information in the signal.

By using genuine models of anatomy more accurate surgical plans may be developed than through statistical modeling.

Terms used herein should be accorded their ordinary meaning in the relevant arts, or the meaning indicated by their use in context, but if an express definition is provided, that meaning controls.

Herein, references to "one embodiment" or "an embodiment" do not necessarily refer to the same embodiment, although they may. Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to." Words using the singular or plural number also include the plural or singular number respectively, unless expressly limited to one or multiple ones. Additionally, the words "herein," "above," "below" and words of similar import, when used in this application, refer to this application as a whole and not to any portions of this application. When the claims use the word "or" in reference to a list of two or more items, that word covers all the following interpretations of the word: any of the items in the list, all the items in the list and any combination of the items in the list, unless expressly limited to one or the other. Any terms not expressly defined herein have their conventional meaning as commonly understood by those having skill in the relevant art(s).

What is claimed is:

1. A computer implemented method for a medical device, comprising:

determining, at a processor of a medical device, whether a credential package stored on a removable authentication device is authentic, wherein the removable authentication device is coupled to the medical device and wherein the medical device comprises the processor and a memory comprising instructions, which when executed by the processor cause the medical device to execute either a user application or a field service technician application, wherein the credential package comprises indications for a plurality of field service technicians;

generating a first graphical indication that the credential package is not authentic and causing the first graphical indication to be displayed on a display coupled to the medical device based on a determination that credential package is not authentic; or verifying, at the processor based on a determination that the credential package is authentic, whether a field service technician attempting to access the medical device is an authorized one of the plurality of field service technicians based on the credential package; and generating a second graphical indication that the field service technician is not authorized and causing the second graphical indication to be displayed on the display based on a determination that field service technician is not authorized; or executing the field service technician application based on a determination that field service technician is authorized.

2. The computer implemented method of claim 1, comprising:

determining, at the processor, whether the authentication device is coupled to the medical device; and determining, at the processor, whether the credential package is stored on the removable authentication device based on a determination that the authentication device is coupled to the medical device.

3. The computer implemented method of claim 2, comprising determining, at the processor, whether the authentication device is coupled to the medical device responsive to a trigger, wherein the trigger is a power cycle of the medical device, a power up of the medical device, or an input received from an input device of the medical device.

4. The computer implemented method of claim 2, comprising determining, at the processor, whether the credential package is authentic based on a determination that the credential package is stored on the removable authentication device.

5. The computer implemented method of claim 1, comprising:

verifying, at the processor based on a determination that the field service technician is authorized, whether the field service technician has a proper role to access the field service technician application; and generating a third graphical indication that the field service technician does not have the proper role and causing the third graphical indication to be displayed on the display based on a determination that field service technician does not have the proper role; or executing the field service technician application based on the determination that field service technician is authorized and a determination that the field service technician has the proper role.

6. The computer implemented method of claim 1, comprising:

identifying, at the processor based on a determination that the field service technician is authorized, a role of the field service technician; and executing a one of a plurality of field service technician applications based on the identified role of the field service technician.

7. The computer implemented method of claim 6, wherein the role of the field service technician is one of a maintenance user role, a developer user role, or a manufacturing user role.

8. The computer implemented method of claim 7, wherein the plurality of field service technician applications comprises one or more of a maintenance user application, a developer user application, and a manufacturing user application.

9. The computer implemented method of claim 1, comprising:

verifying, at the processor based on a determination that the field service technician is authorized, whether the field service technician has a proper training to access the field service technician application; and generating a third graphical indication that the field service technician does not have the proper training and causing the third graphical indication to be displayed on the display based on a determination that field service technician does not have the proper training; or executing the field service technician application based on the determination that field service technician is authorized and a determination that the field service technician has the proper training.

10. The computer implemented method of claim 1, wherein the credential package is signed by a private key from an asymmetric key pair, and wherein determining, at the processor, whether the credential package is authentic comprising verifying the authenticity of the credential package using a public key from the asymmetric key pair.

11. The computer implemented method of claim 1, wherein the credential package is encrypted by a public key from an asymmetric key pair, and wherein determining, at the processor, whether the credential package is authentic comprising decrypting the credential package using a private key from the asymmetric key pair.

12. The computer implemented method of claim 1, wherein the memory comprises operating system (OS) instructions, which when executed by the processor cause the medical device to execute the OS, wherein the OS comprises a secure shell (SSH) and wherein verifying, at the processor, whether the field service technician is authorized comprises:

receiving at least a password from the field service technician; and establishing an SSH connection to the OS based in part on the password.

13. The computer implemented method of claim 12, comprising determining that the field service technician is authorized based on whether the SSH connection to the OS is successful.

14. An apparatus for a medical device, comprising:

a processor; and memory coupled to the processor, the memory comprising instruction that when executed by the processor cause the medical device to:

determine whether a credential package stored on a removable authentication device is authentic, wherein the removable authentication device is coupled to the medical device and wherein the medical device comprises the processor and a memory comprising instructions, which when executed by the processor cause the medical device to execute either a user application or a field service technician application, wherein the credential package comprises indications for a plurality of field service technicians;

generate a first graphical indication that the credential package is not authentic and causing the first graphical indication to be displayed on a display coupled to the medical device based on a determination that credential package is not authentic; or verify whether a field service technician attempting to access the medical device is an authorized one of the plurality of field service technicians based on the credential package based on a determination that the credential package is authentic; and generate a second graphical indication that the field service technician is not authorized and causing the second graphical indication to be displayed on the display based on a determination that field service technician is not authorized; or execute the field service technician application based on a determination that field service technician is authorized.

15. The apparatus of claim 14, the instructions when executed by the processor further cause the medical device to:

verify whether the field service technician has a proper role to access the field service technician application based on a determination that the field service technician is authorized; and generate a third graphical indication that the field service technician does not have the proper role and causing the third graphical indication to be displayed on the display based on a determination that field service technician does not have the proper role; or execute the field service technician application based on the determination that field service technician is authorized and a determination that the field service technician has the proper role.

16. The apparatus of claim 14, the instructions when executed by the processor further cause the medical device to:

identify a role of the field service technician based on a determination that the field service technician is authorized; and execute a one of a plurality of field service technician applications based on the identified role of the field service technician.

17. The apparatus of claim 14, wherein the memory comprises operating system (OS) instructions, which when executed by the processor cause the medical device to execute the OS, wherein the OS comprises a secure shell (SSH) and wherein the instructions, when executed by the processor further cause the medical device to:

receive at least a password from the field service technician; and establish an SSH connection to the OS based in part on the password.

18. A computer-readable storage device comprising instruction, which when executed by a processor of a medical device cause the medical device to:

determine whether a credential package stored on a removable authentication device is authentic, wherein the removable authentication device is coupled to the medical device and wherein the medical device comprises the processor and a memory comprising instructions, which when executed by the processor cause the medical device to execute either a user application or a field service technician application, wherein the credential package comprises indications for a plurality of field service technicians;

generate a first graphical indication that the credential package is not authentic and causing the first graphical indication to be displayed on a display coupled to the medical device based on a determination that credential package is not authentic; or verify whether a field service technician attempting to access the medical device is an authorized one of the plurality of field service technicians based on the credential package based on a determination that the credential package is authentic; and generate a second graphical indication that the field service technician is not authorized and causing the second graphical indication to be displayed on the display based on a determination that field service technician is not authorized; or execute the field service technician application based on a determination that field service technician is authorized.

19. The computer-readable storage device of claim 18, the instructions when executed by the processor further cause the medical device to:

identify a role of the field service technician based on a determination that the field service technician is authorized; and execute a one of a plurality of field service technician applications based on the identified role of the field service technician.

20. The computer-readable storage device of claim 18, wherein the memory comprises operating system (OS) instructions, which when executed by the processor cause the medical device to execute the OS, wherein the OS comprises a secure shell (SSH) and wherein the instructions when executed by the processor further cause the medical device to:

receive at least a password from the field service technician; and establish an SSH connection to the OS based in part on the password.

* * * * *